United States Patent
Yamazawa et al.

(10) Patent No.: US 7,758,792 B2
(45) Date of Patent: Jul. 20, 2010

(54) ARTIFICIAL BONE FORMING METHOD BY POWDER LAMINATION METHOD

(75) Inventors: Kenji Yamazawa, Wako (JP); Masahiro Anzai, Wako (JP); Hideo Yokota, Wako (JP); Shigeki Suzuki, Tokyo (JP)

(73) Assignees: Riken, Saitama (JP); New X-national Technology K.K., Tokyo (JP)

( * ) Notice: Subject to any disclaimer, the term of this patent is extended or adjusted under 35 U.S.C. 154(b) by 1044 days.

(21) Appl. No.: 10/595,077

(22) PCT Filed: Jul. 28, 2004

(86) PCT No.: PCT/JP2004/010701

§ 371 (c)(1),
(2), (4) Date: Jul. 10, 2006

(87) PCT Pub. No.: WO2005/011536

PCT Pub. Date: Feb. 10, 2005

(65) Prior Publication Data

US 2007/0181239 A1  Aug. 9, 2007

(30) Foreign Application Priority Data

Jul. 31, 2003  (JP) .............................. 2003-284055

(51) Int. Cl.
*B29C 41/02* (2006.01)
(52) U.S. Cl. .................. 264/308; 264/102; 264/113
(58) Field of Classification Search .................. None
See application file for complete search history.

(56) References Cited

U.S. PATENT DOCUMENTS

| 5,204,055 | A | 4/1993 | Sachs et al. |
| 5,902,441 | A | 5/1999 | Bredt et al. |
| 6,322,728 | B1 | 11/2001 | Brodkin et al. |
| 6,375,874 | B1 | 4/2002 | Russell et al. |
| 7,435,367 | B2 * | 10/2008 | Oriakhi ...................... 264/113 |
| 7,455,804 | B2 * | 11/2008 | Patel et al. .................. 264/460 |
| 2002/0064745 | A1 | 5/2002 | Schulman et al. |

(Continued)

FOREIGN PATENT DOCUMENTS

JP  09324203  12/1997

(Continued)

OTHER PUBLICATIONS

Yasuo Ueda et al., "Rapid Prototyping no Iryo Bunya eno Oyo", Hokkaio Journal of Dental Science, Jun. 15, 2003, pp. 3-13, vol. 24, No. 1 (no translation available).

(Continued)

*Primary Examiner*—Mary Lynn F Theisen
(74) *Attorney, Agent, or Firm*—Griffin & Szipl, P.C.

(57) ABSTRACT

An artificial bone forming method, comprising a) a powder layer forming step (32) for forming, into a flat powder layer (6), a powder bone material (5) having biocompatibility and hardening by hydration, b) a partial hardening step (34) for jetting an aqueous solution (7) with biocompatibility to a part of the powder layer to harden a jetted portion (6a) by hydration, and c) an artificial bone forming step (36) for repeating the steps a) and b) for lamination to form a specified artificial bone (9) of a predetermined three-dimensional structure in which the hardened portions (6a) are connected to each other.

12 Claims, 5 Drawing Sheets

U.S. PATENT DOCUMENTS

2003/0030170 A1* 2/2003 Abe et al. .................. 264/113
2003/0042641 A1* 3/2003 Abe et al. .................. 264/40.1

FOREIGN PATENT DOCUMENTS

| JP | 2003070816 | 3/2003 |
| JP | 2003135583 | 5/2003 |
| JP | 2004042546 | 2/2004 |
| JP | 2004069403 | 3/2004 |
| JP | 2004202126 | 7/2004 |

OTHER PUBLICATIONS

Yamazawa et al., "Fabrication of multicolor model by color RP machine", 19th Rapid Prototyping Symposium, 2000, pp. 63-65. (no translation available).

Yamazawa et al., Making to substance of the Molecular Structure by Layered Manufacturing (identified in the specification as "Substantiation of molecular structure by lamination forming method").

International Search Report issued in corresponding application No. PCT/JP2004/010701 completed Oct. 15, 2004 and mailed Nov. 2, 2004.

* cited by examiner

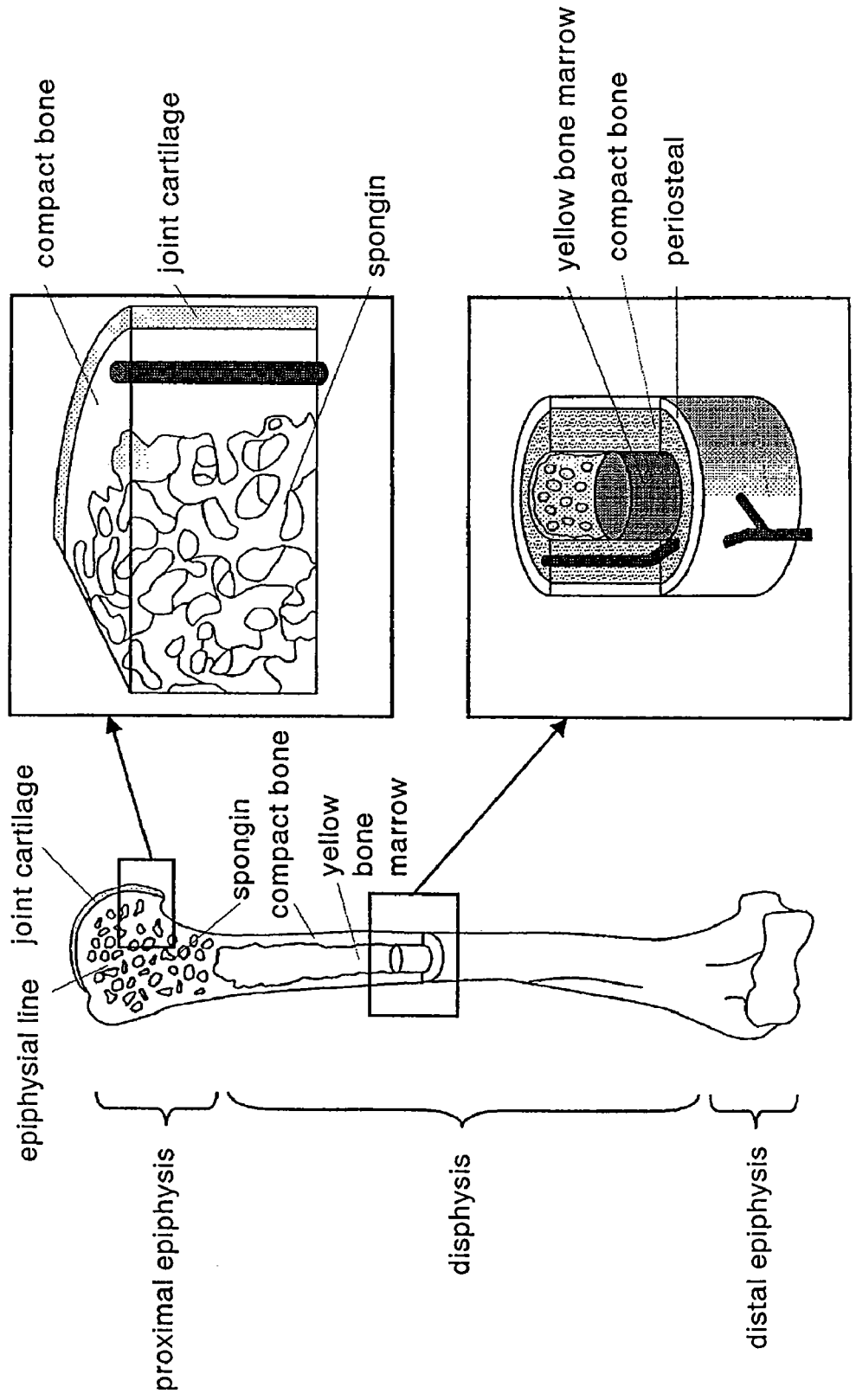

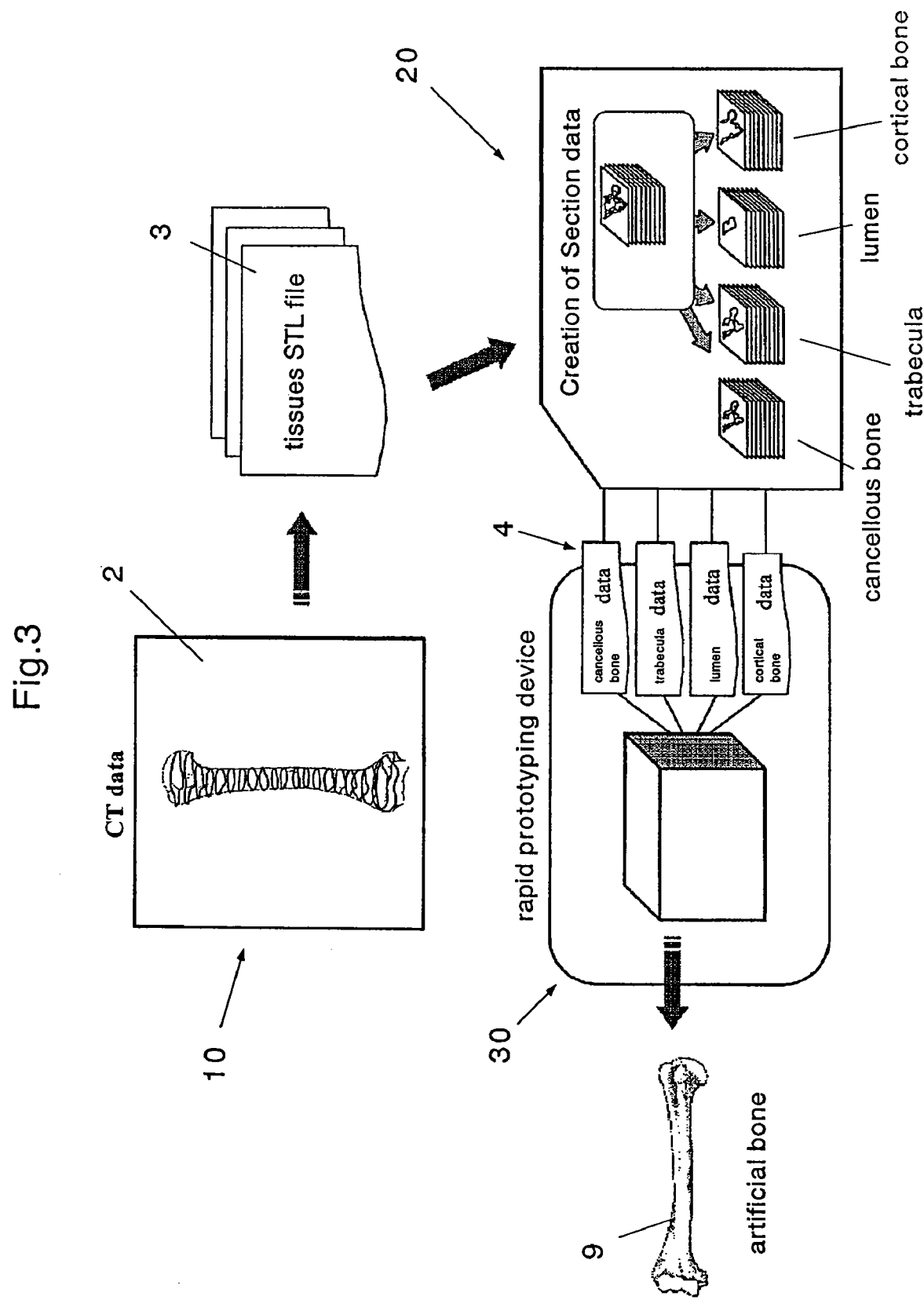

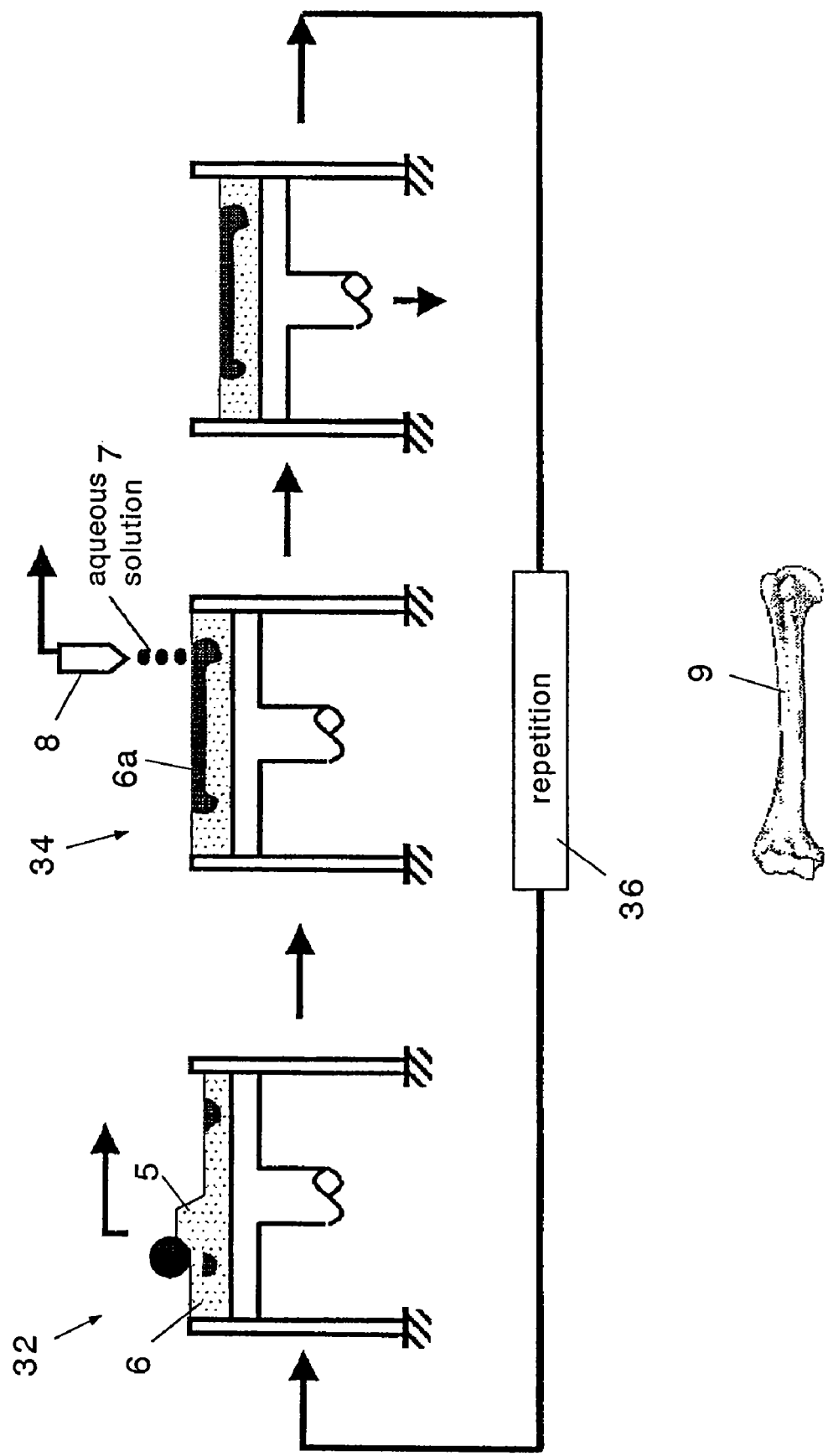

ARTIFICIAL BONE FORMING METHOD BY POWDER LAMINATION METHOD

This is a National Phase Application in the United States of International Patent Application No. PCT/JP2004/010701 filed Jul. 28, 2004, which claims priority on Japanese Patent Application No. 284055/2003, filed Jul. 31, 2003. The entire disclosures of the above patent applications are hereby incorporated by reference.

BACKGROUND OF THE INVENTION

1. Technical Field of the Invention

The present invention relates to an artificial bone forming method by a powder lamination method.

2. Description of the Related Art

Rapid prototyping is called a lamination forming method which laminates a sectional shape of an object to create a three-dimensional object. A lamination method (powder fixing method) which is a kind of rapid prototyping and uses powder as materials is disclosed or filed (not laid-open) in each of Nonpatent Documents 1, 2 and Patent Documents 1 to 5.

Further, means for artificially forming eyeballs, teeth, bones and the like which constitute a living organism by using the powder lamination method are disclosed or filed (not laid-open) in Patent Documents 6 to 9.

"Solid color copying and method" (not laid-open) of the Patent Document 6 includes a sample section imaging step (A) of sequentially extruding a sample in a predetermined direction to cut it, thereby imaging a two-dimensional image of a cut section, a data processing step (B) of calculating a three-dimensional internal structure of the sample from the two-dimensional image to convert it into data which can be subjected to color rapid prototyping, and a solid color model building step (C) of building a solid color model by using a color rapid prototyping device.

"Mass production of dental restoration by solid free-form fabrication methods" of the Patent Document 7 includes (a) forming a layer of a ceramic or composite material, (b) adding a binder to the layer, (c) repeating (a) and (b) many times to form a number of interconnected layers into a shape of a tooth prosthesis, and (d) reinforcing the formed material to fabricate a tooth prosthesis.

"Mass production of shells and models for dental restoration produced by solid free-form fabrication methods" of the Patent Document 8 includes (a) preparing a shell shape of a tooth prosthesis by using digital data, (b) forming a layer of a polymer material, and (c) repeating (b) many times to form a number of interconnected layers into a shell shape based on the digital data.

"Artificial bone forming method" of the Patent Document 9 includes (a) a step for transporting a powder material for a living organism and a liquid material through different flow paths to the vicinity of a nozzle tip of a jetting device, (b) a step for jetting a mixture of the living organism powder material and the liquid material from a nozzle of the jetting device to a solid surface, and depositing the mixture of the living organism powder material and the liquid material on the solid surface to form a layer, and (c) a step for further jetting the mixture of the living organism powder material and the liquid material to the layer to repeat lamination of deposition surfaces of the mixture, thereby stacking a plurality of layers to form a bone three-dimensional structure into a solid shape.

Nonpatent Document 1: pp. 63 to 65, "Fabrication of multicolor model by color RP machine" by Yamazawa, Anzai and et al., 19th Rapid Prototyping Symposium, 2000

Nonpatent Document 2: "Substantiation of molecular structure by lamination forming method" by Yamazawa, Anzai and et al.

Patent Document 1: Three-dimensional printing techniques", specification of U.S. Pat. No. 5,204,055

Patent Document 2: "Method of three dimensional printing", specification of U.S. Pat. No. 5,902,411

Patent Document 3: "Method and apparatus for prototyping a three dimensional object", specification of U.S. Pat. No. 6,375,874

Patent Document 4: "Three-dimensional shape forming method by powder lamination method", JP A 9-324203

Patent Document 5: "Lamination forming method of functional material" not laid-open, specification of JP A 2002-205825

Patent Document 6: "Solid color copying method and device" not laid-open, specification of JP A 2002-226859

Patent Document 7: "Mass production of dental restoration by solid free-form fabrication methods", specification of U.S. Pat. No. 6,322,728

Patent Document 8: "Mass production of shells and models for dental restoration produced by solid free-form fabrication methods", specification of U.S. Patent No. 20020064745

Patent Document 9: "Artificial bone forming method" not laid-open, specification of JP A 2002-377836

Conventionally, an artificial bone has been made of a metallic material such as stainless or titanium alloy, abrasion-resistant plastic, or the like, and used for a bone replacement technology. Such an artificial bone acts for a dysfunctional joint. However, the metallic material or the abrasion-resistant plastic has had a problem that long-time use is impossible because of a change with time such as abrasion, corrosion or swelling.

Recently, on the other hand, it has been made possible to form an artificial bone similar in shape to a target bone by putting ceramics in a mold to burn it or shaving it off from a burned block. In the case of such an artificial bone, however, its appearance structure alone is similar, and there remains a problem regarding biocompatibility or absorption substitution while no change with time such as abrasion, corrosion, or swelling occurs.

SUMMARY OF THE INVENTION

The present invention has been developed to solve the aforementioned problems. That is, it is an object of the present invention to provide an artificial bone forming method which can form an artificial bone having a shape similar to that of a target bone, and a nature and components similar to those of a bone of a living organism, and implantable in substitution technology.

According to the present invention, there is provided an artificial bone forming method by a powder lamination method, comprising a) a powder layer forming step for forming, a powder bone material having biocompatibility and hardening by hydration, into a flat powder layer, b) a partial hardening step for jetting an aqueous solution with biocompatibility to a part of the powder layer to harden a jetted portion by hydration, and c) an artificial bone forming step for repeating the steps a) and b) for lamination to form a specified artificial bone of a predetermined three-dimensional structure in which the hardened portions are connected to each other.

According to a preferable embodiment of the present invention, the powder bone material is constituted of an inorganic component such as calcium phosphate and other bone components, and the aqueous solution is a liquid mixture or a suspension of water and a water-soluble biopolymer which is a component derived from a living organism.

The powder bone material is a calcium salt such as calcium phosphate, hydroxyapatite, human bone, animal bone, alumina, collagen, polylactic acid, a copolymer of polylactic acid and polyglycolic acid, or a mixture thereof.

Furthermore, the aqueous solution is a liquid mixture or a suspension of water and soluble collagen, proteoglucan, linkprotein, sodium tartrate, a pH adjuster, a bone growth factor, fibrin, PRP (Platelet-Rich Plasma), a polysaccharide, an amino acid polymer, polylactic acid, a copolymer of polylactic acid and polyglycolic acid, or a mixture thereof.

Furthermore, two or more kinds of liquid mixtures which react with each other in a liquid layer to bring about a hardening reaction are put in separate vessels, and they are jetted through a plurality of ink jet nozzles so as to be mixed and hardened at a jetting portion.

Furthermore, a component which further promotes a crosslinking reaction or polymerization of a polymeric component of the artificial bone is put in a vessel different from a vessel for a living material to be reacted or polymerized, and the component is jetted through another ink jet nozzle to be mixed at an intended position.

For example, a mixture of an ethylene silicate solution and a catalyst is jetted through two different nozzles to hydrolyze ethylene silicate in the state of a hydroxyapatite powder layer, thereby preparing and hardening a polymer of the silicate.

Furthermore, it is desirable that after the step c), the method comprises d) an artificial bone reinforcing step for discharging a gas contained in the artificial bone to further reinforce the hardened portions by a reaction by using a change in pressure. Since a suspension of collagen or polylactic acid has a high viscosity, its penetration by capillary phenomenon is difficult. In consequence, to positively accelerate the penetration of the suspension into a bone structure, it is desirable that a reduced pressure treatment or a pressure treatment is carried out to promote the replacement of air therein with the solution to be hardened.

Furthermore, after the artificial bone reinforcing step or the step c), a hardening reaction is promoted for the formed artificial bone directly under high-temperature and high-pressure water vapor or under a dry high temperature in an autoclave.

Furthermore, it is preferable to carry out a high-temperature heat treatment in a vacuum state or an oxygen-free atmosphere to induce a reaction between biopolymers of an artificial bone formed by mixing the biopolymers, a reaction with other components, or melting.

The strength of the collagen increases by drying the collagen and treating it in an atmosphere of 120 to 130° C. to polymerize it. Moreover, the strength and impact strength of polylactic acid in the bone structure increase by heating it at a melting point of the polylactic acid or more to melt inorganic bone components and to bond particles.

Furthermore, according to the present invention, there is provided an artificial bone forming method by a powder lamination method, comprising a) a two-dimensional data creating step for sequentially moving a target bone in a predetermined direction to create two-dimensional data of a cut section, b) a tissue data processing step for creating data to be subjected to rapid prototyping for a plurality of tissues constituting a bone from the two-dimensional data, and c) an artificial bone forming step for forming an artificial bone constituted of a plurality of tissue structures by using a rapid prototyping device.

The tissue data is constituted of a plurality of data selected from a cancellous bone, a bone trabecula, a lumen, and a cortical bone.

According to the method of the present invention, the bone material having biocompatibility and the aqueous solution alone are used. Hence, it is possible to form an artificial bone having a nature and components similar to those of a bone of a living organism, and implantable in substitution technology.

The artificial bone reinforcing step is taken, and the hardening reaction is promoted in the autoclave or the heating chamber when necessary. Hence, it is possible to provide strength equal to that of a bone of a living organism, and to leave the artificial bone in the living organism for a long time.

Furthermore, based on the target bone, the data constituted of the plurality of data selected from the cancellous bone, the bone trabecula, the lumen, and the cortical bone, and subjected to rapid prototyping is created, and the artificial bone having the plurality of organization structures is formed by using the rapid prototyping device. Hence, it is possible to form an artificial bone having a shape similar to that of a target bone, and a similar internal structure.

Other objects and advantageous features of the present invention will become apparent upon reading of the following detailed description made with reference to the accompanying drawings.

BRIEF DESCRIPTION OF THE DRAWINGS

FIG. 1 is a schematic diagram showing a structure of a bone;

FIG. 3 is a diagram showing a flow of data by an artificial bone forming method of the present invention;

FIG. 4 is a diagram showing a powder lamination process by the artificial bone forming method of the present invention.

DESCRIPTION OF THE PREFERRED EMBODIMENT

Figure 2A:
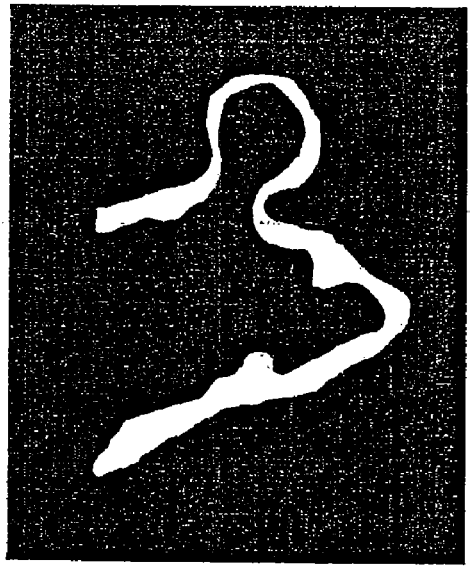
FIGS. 2A to 2D are diagrams showing sectional structures of bones.

The preferred embodiment of the present invention will be described below with reference to the accompanying drawings. Throughout the drawings, similar portions are denoted by similar reference numerals, and repeated explanation will be avoided.

FIG. 1 is a schematic diagram showing a structure of a bone. As shown, even if it were animal or human bones, bones are generally classified into a proximal epiphysis, a distal epiphysis, and a diaphysis therebetween which constitute a joint. The epiphysis is constituted of a joint cartilage, a compact bone, a spongin, and an epiphysial line from a surface. The diaphysis is constituted of a periosteal, a compact bone, a yellow bone marrow, and the like from a surface.

Figure 2B:
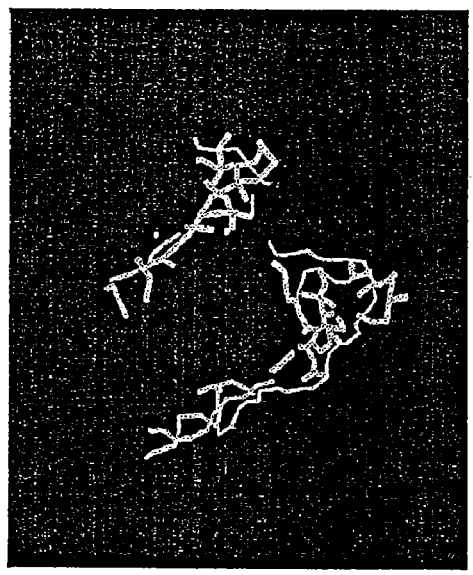
Figure 2C:
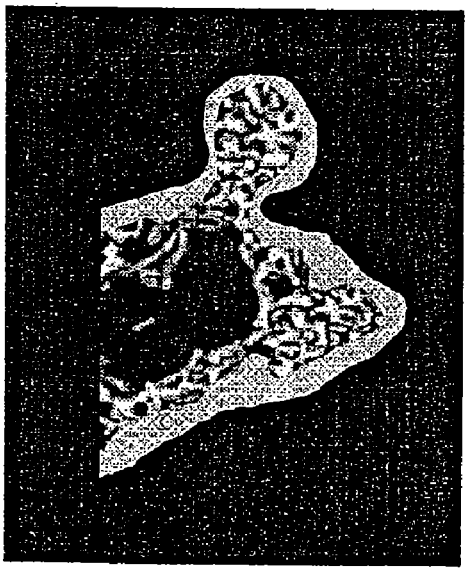
Figure 2D:
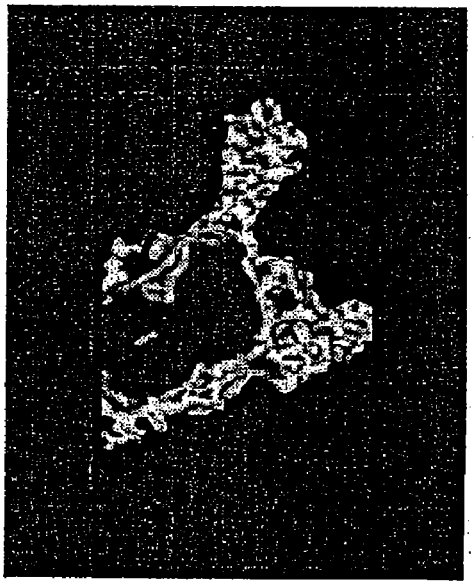

FIGS. 2A to 2D are images showing sectional structures of bones. In the drawings, FIG. 2A is an entire image showing a thighbone, a cancellous bone, a cortical bone, and a lumen, FIG. 2B shows a cortical bone, FIG. 2C shows a thighbone cancellous bone, and FIG. 2D shows a skeletal line and a trabecular thickness.

It can be understood from FIGS. 1 and 2A to 2D that the bone is not homogeneous as a whole, and constituted of a plurality of tissues (cancellous bone, trabecula, lumen, cortical bone, and the like).

FIG. 3 shows a flow of data by an artificial bone forming method of the present invention. In the drawing, the artificial bone forming method of the invention includes a two-dimensional data creating step 10, a tissue data processing step 20, and an artificial bone forming step 30.

In the two-dimensional data creating step 10, a target bone (animal or human bone) is sequentially moved in a predetermined direction to create two-dimensional data 2 of a cut section. In this step, the bone may be cut by actually using a cutter, or data may be nondestructively obtained by CT scanning or the like. The obtained two-dimensional data 2 will be referred to as CT data in this example.

In the tissue data processing step 20, data 4 to be subjected to rapid prototyping for a plurality of tissues constituting a bone is created from the two-dimensional data 2. In this example, an STL file 3 is formed for each tissue from the CT data 2, and then tissue data 4 (cancellous bone data, trabecula data, lumen data, and cortical bone data) classified into a cancellous bone, a trabecula, a lumen, and a cortical bone is created from each slice data (CT data 2).

In the artificial bone forming step 30, an artificial bone 9 constituted of a plurality of tissue structures is formed by using a rapid prototyping device.

FIG. 4 shows a powder lamination process by the artificial bone forming method of the present invention. This powder lamination process corresponds to the artificial bone forming step 30.

The powder lamination process includes a powder layer forming step 32, a partial hardening step 34, and an artificial bone forming step 36.

In the powder layer forming step 32, a powder bone material 5 having biocompatibility and hardening by hydration is formed into a flat powder layer 6.

In the partial hardening step 34, an aqueous solution 7 (hardening liquid) having biocompatibility is jetted to a part of the powder layer 6 to harden a jetted portion 6a by hydration.

In the artificial bone forming step 36, the powder layer forming step 32 and the partial hardening step 34 are repeated for lamination to form an artificial bone 9 having a desired three-dimensional structure in which the hardened portions 6a are connected to each other.

Further, according to the method of the invention, in an artificial bone reinforcing step (not shown), the artificial bone 9 formed in the artificial bone forming step 36 is held under reduced pressure, a gas contained therein is discharged, and the hardened portion is reinforced more by hydration. Preferably, after the artificial bone reinforcing step, a hardening reaction of the formed artificial bone is promoted under high-temperature and high-pressure water vapor in an autoclave.

Figure 5:
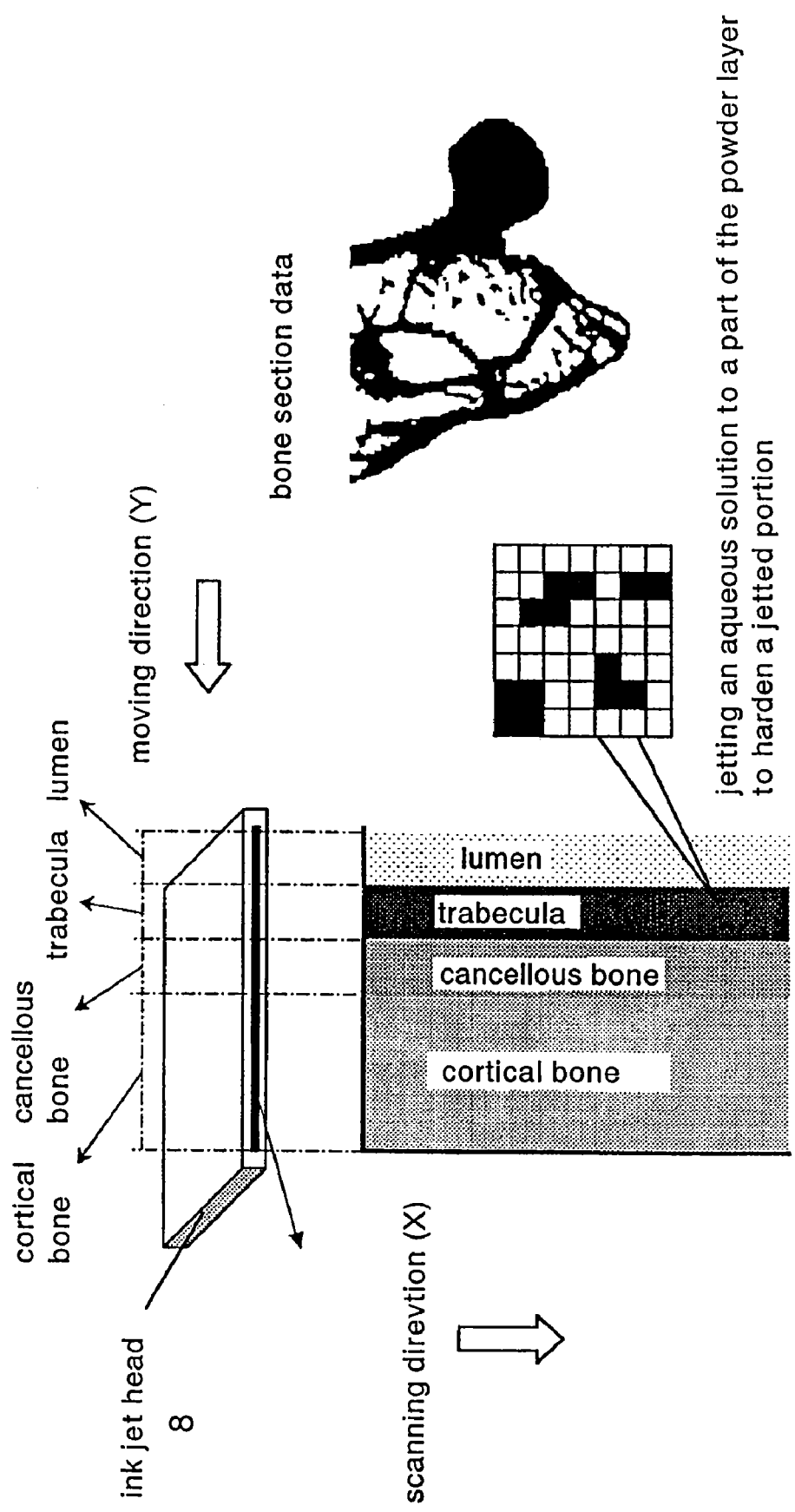
FIG. 5 is a block diagram of an ink jet head compatible to the structure of the bone.

FIG. 5 is a block diagram of an ink jet head compatible to a bone structure. This ink jet head 8 is constructed in such a manner that a plurality of nozzles are serially arranged in a direction orthogonal to a scanning direction (X), and a jetting amount of a hardening liquid (aqueous solution 7) corresponding to a lumen, a trabecula, a cancellous bone, and a cortical bone is changed to control a fixed portion and its hardness.

Two or more kinds of liquid mixtures which react with each other in a liquid layer to bring about a hardening reaction are preferably put in separate vessels, and jetted from the plurality of ink jet nozzles 8 to be mixed and hardened at a jetting portion. Further, a component which promotes a crosslinking reaction or polymerization of a polymeric component of the artificial bone is put in a vessel different from that of a living material to be reacted or polymerized, jetted from a different ink jet nozzle to be mixed at an intended position.

In a bone tissue of a living organism, a hard inorganic substrate made of a hydroxyapatite (phosphorus hydroxide ashstone) crystal, and chondroitin sulfate (sulfate-coupled type proteoglycan) are buried in a collagen I type to form a matrix. For cells, there are an osteoblast and a bone cell. The former actively produces organic bone substrates, and limes are deposited thereon to form lamellar inorganic substrates. The bone cell is a cell in which the osteoblast is buried in a bone substrate made by itself to lose its bone substrate forming function, and the cell is located in a minimum cavity. As another kind of cell, there is a multinucleated osteoclast, which causes bone substrate melting. As in the case of a cartilage tissue, the bone tissue is covered with a periosteal which is a connective tissue, and strongly connected to another bone tissue by Sharpie fiber (type-I collagen).

According to the present invention, a special bioactive artificial bone material (powder bone material 5) which reacts with water to be hardened is used to form the artificial bone 9 in three-dimensional lamination without using a burning process. Reactive components are separately jetted for the purpose of improving biocompatibility, absorption substitution for a living organism, and strength to form the bone, whereby an artificial bone having a function, components and a shape similar to those of a bone of a living organism, impossible to be obtained by a normal reaction method, can be formed.

According to a feature of the forming method, as a bone internal structure (trabecula, cancellous bone) can be reproduced, biocompatibility is high not only for components but also for a structure, and substitution for the bone of the living organism is fast.

Furthermore, by burying the bone cell in a porous portion of the bone internal structure, it is possible to apply the artificial bone as a cell support (scaffold) for medical osteoclassis.

Hereinafter, the present invention will be described more in detail.

1) By the present invention, two-dimensional data obtained from a CT image of X-ray, MRI or the like is subjected to CAD conversion, and an artificial bone for implantation is formed by a three-dimensional lamination forming device in a CAM process. This forming method must satisfy some conditions.

a) For a particle size of a powder (powder bone material 5) of a powder layer 6, an average particle diameter is preferably 10 microns or less from the standpoint of forming strength and hardening reaction time. Hardening time is faster as a particle is smaller, and strength after hardening tends to increase. However, as crushing into particles of less than 100 nanometers is extremely difficult, an average particle diameter of 100 nanometers or more is used.

When powders having two kinds of particle sizes in which medium values are apart from each other by three times as much as a particle size distribution to form an artificial bone, a filling density increases to reduce porosity. Accordingly, high physical strength is obtained.

b) A liquid phase (aqueous solution 7) to be jetted is mainly constituted of water soluble components. For example, an aqueous solution of soluble collagen, a pluteogulycan, a link protein, sodium tartrate and a buffer component for pH adjustment is prepared to have such a viscosity that the solution can be jetted through the ink jet nozzle.

c) A roller is generally used for flattening the powder layer. To form a flat surface, a particle size of a powder, a rotational speed of the roller, and a moving speed must be adjusted.

d) To increase strength of an artificial bone after a forming operation, it is necessary to assist a reaction between formed hardening components. During the forming operation, a gas is contained in the formed object, and a reaction between a powder phase and a liquid phase by jetting may not be enough. Thus, a reaction must be completed by addition after the forming.

Basically, an object is dipped in a liquid of the same component as that of a jetted liquid layer or an artificial body liquid, and pressure (reduced pressure) is applied by a vacuum pump to remove a gas from the inside, thereby assisting infiltration of a liquid layer component therein.

2) For the powder layer 6, a water insoluble inorganic component having high biocompatibility, especially a calcium compound such as calcium phosphate having a nature of being hardened by hydration, is preferable. Other water insoluble or hardly soluble components are mixed as fine particles to form a powder bed used during jetting forming.

3) When the artificial bone 9 is formed by the jetted liquid 7 from the ink jet nozzle 8, a jetted solution layer is made of a component for assisting polymerization, crosslinking, connection and the like with the water soluble component of the bone of the living organism. Further, as pH at the time of hardening is important for the inorganic component, a pH buffer material must be added.

A representative bone component of a living organism is collagen. There are known eighteen kinds of collagen types (collagen families). Each type has an organ idiosyncrasy. For example, I-type collagen is mainly present in a skin, a bone, a tendon, and the like, II-type collagen is mainly present in a cartilage, a corpus vitreum, and the like, II-type collagen is mainly present in a blood, a skin, and the like, and IV-type collagen is mainly present in a basilar membrane, and the like. Forming targets of a bone and a cartilage are I and II type collagens.

The pluteogulycan as another bone component of the living organism is a generic term of a molecule in which glycosaminoglycan is covalent bonded to a protein, and it is a main component of a cell surface and out-of-cell matrix. The glycosaminoglycan is classified, in accordance with its skeleton structure, into chondroitin sulfate, deltaman sulfate, heparin sulfate, heparin, ketaran sulfate, and hyaluronic acid.

As another component, link protein is known to increase strength of the bone and the cartilage. Fibrin, platelet-rich blood serum (PRP), various polysaccharides, an amino-acid polymer, and the like can increase the strength of the bone because of high biocompatibility.

The artificial bone can be formed by putting a bone cell growth factor or the like in the liquid phase for the purpose of quickening substitution of the formed artificial bone material for a bone cell. Especially, a bone forming factor (BMP) has a strong bone reproduction inducing ability. As other cytokines to promote bone cell growth and substrate growth, there are a basic fibroblast growth factor (b-FGF), a transforming growth factor (TGFβ), an insulin growth factor (IGF-1), and the like.

4) Aggregation or precipitation occurs when the liquid phase components for bone formation are mixed, causing a reduction in forming performance or a trouble in jetting from the nozzle. In this case, components which react with each other are stored in different vessels, and separately jetted from the circuit and the nozzle during formation to be mixed on the target powder layer. The bone components of the living organism coagulate and react with each other to from a matrix or a complex. To reproduce such a complex component environment, a plurality of liquid phases must be physically separated, and a reaction thereof must be mechanically controlled to bring about a reaction at a target place.

5) To increase strength and tenacity of the formed artificial bone, it is useful to form a polymer by polymerization of biomolecules and a meshed structure by crosslinking. A polymerization agent or a crosslinking agent is put in the liquid phase jetted from the nozzle to improve physical properties of the artificial bone after the formation, whereby an artificial bone similar to a bone of a living organism can be formed.

6) Hydration hardening reaction of the inorganic component of the formed artificial bone is promoted by high steam pressure at a high temperature. The artificial bone is processed at a sterilizing cycle in a sterilization autoclave to greatly shorten hardening time.

Furthermore, reaction processing is executed in an atmosphere of a high-temperature dry state for a long time in a drying process of the autoclave to crosslink, and polymerize the biopolymers in the artificial bone to react with each other, thereby improving the strength and the tenacity more. Because of the process of a higher temperature and a longer time than a normal sterilization process, a sterile state of the artificial bone is simultaneously established.

Example 1

For a powder layer of a three-dimensional lamination forming device equipped with a powder flattening roller, α-TCP calcium phosphate fine particles were used, sodium tartrate, and a chondroitin sodium sulfate aqueous solution were used for an ink jet liquid layer, and a liquid layer is jetted onto the powder after flattening into a thickness of 100 microns by the roller to draw a two-dimensional image. This work was repeated to stack powder layers, thereby forming a solid object.

Unnecessary unhardened powders were removed from the formed object, the object was dipped in the same aqueous solution as that of the ink jet liquid layer to additionally harden its inside, and pressure was reduced in a closed vessel by a vacuum pump.

After bubbles were removed from the formed object for substitution with the liquid layer by the pressure reduction processing, the object was left still at about a room temperature for three days to finish a hardening reaction. As a result, an artificial bone 9 having a desired three-dimensional structure was formed.

Example 2

Soluble 0.2% butacollagen is mixed with a solution containing sodium tartrate and chondroitin sodium sulfate to produce a deposited object in an ink jet liquid phase by using the same device and the same powder layer as those of the Example 1, and thus a collagen contained artificial bone was formed by jetting from a vessel and a nozzle of a different system. By this method, production of deposited objects was prevented.

Example 3

During forming by putting collagen and a hyaluronic acid in a liquid phase, a small amount of a glyoxal solution was jetted from a vessel and a nozzle of a different system to form an artificial bone. Then, curing of hydration hardening reaction and crosslinking reaction was carried out, and the bone was left in agitation purified water for twenty four hours to remove unreacted articles about three days later.

Example 4

Using hydroxyapatite powders of an average particle diameter of 30 microns for the same device as that of the Example 1, ethylsilicate and a catalyst solution (hardening agent) were jetted to the hydroxyapatite powder layer at a weight ratio of 30:1 to be hardened. A complex of hydroxyapatite and silica was formed, and the dry hardened object was dipped in a hardening agent B (in post processing agent) for about 30 minutes to form a glass shiny object.

When 3-hour burning was executed again at about 800° C. after the drying, a silica polymerization degree was increased to improve strength.

Example 5

As in the case of the Example 1, a lamination was formed by using mixed powders in which calcium phosphate raw material powders and polyactic acid powders were mixed at a weight ratio of 70:30. After the formed object was dried to remove water, 3-hour heating was carried out at 140° C. As a result, the melted polyactic acid worked as a binder between calcium phosphate particles to form an artificial bone having not only high compression strength but also high bending strength.

Example 6

An artificial bone formed by the same method as that of the Example 2 was put in a sterilization bag, put in an autoclave to remove air from the artificial bone formed object in an air removing step, and high-temperature and high-humidity processing was carried out at a 121° C. for about one hour (mainly promotion of hydration hardening reaction). After removal of internal vapor, processing was carried out for about 3 hours in a drying step of 130° C. (promotion of collagen crosslinking reaction).

For a cartilage matrix, aggrecan (cartilage puluteoglycan) of a large molecular weight was connected to hyaluron, and linkprotein which is glycoprotein to 40 kd reinforced the connection of both to prepare a porous matrix made of gelatin and hydroxyapatite (HA). This matrix was prepared by using a small amount of carbodiimide (EDCI) for a crosslinking agent, and dipping a water soluble sponge of gelatin and HA in 90% (w/v) acetone/water mixed solution. This sponge type biomaterial was formed as a cover for a wound or a tissue engineering scaffold.

A complex of HA and collagen was prepared by coagulating two components in an aqueous acetic acid solution, and crosslinking them through glyoxal or exess-rich acetic acid starch dialdehyde.

Another composition of HA and collagen was prepared by crosslinking a dry HA/collagen coagulated object through polyethylene oxide and hexamehylene isocyanate.

A complex material of hydroxyapatite and collagen-HA was prepared by adding hydroxyapatite particles in an HA solution, and mixing them with a collagen fiber suspended in water. A final product constituted of a composition of hydroxyapatite 90%, collagen 9.2%, and HA 0.8% (w/v) has biocompatibility and mechanical strength, and was used as a filler for a bone loss.

There are materials having multiple and regularly arranged carboxyl groups. These are full glycodxamionoglycan, pectin, alginic acid, carboxylmethyl cellulose (CMC), and polyacrylic acid. When these polymers are blended with HA and crosslinking chemicals described below are applied, a complex and new-dimensional hydrogel containing HA by chemical modification is obtained.

Properties of alginic acid gel formation (by chelated metal formation) promoted formation of a hydrogen when it was blended with HA. Accordingly, the alginic acid HA gel was prepared by diffusing calcium ions in an alginic acid-HA mixture. A gel having an alginic acid and Ha ratio of 1:1 exhibited sufficient mechanical characteristics. This composition is applied for a joint surgical operation as a carrier of a biocompatible polymer and because it is stable in a bone liquid.

An HA containing copolymer has been prepared to optimize mechanical strength and to obtain conditions optimal for medicine delivery and stability in a living organism. For example, a comb-shaped polymer amphoteric electrolyte copolymer having poly(L-lysine) (PLL) as a main chain, a connected part with a DNA, and an HA chain having a cell specific ligand as a side chain was prepared by targeting a sinusoidal inner skin cell of the liver. An HA reduction end and a PLL ϵ-amino group were covalent-bonded by a reduction amino reaction using sodium cyanoborohydride to obtain a comb-shaped copolymer (PLL-graft HA). This polycationic PLL skeleton was selectively connected with a polyanionic DNA even when the HA chain was present. Further, the PLL-graft-HA-DNA complex may have formed a multilayer structure whose outer side was surrounded with hydrated HA free of hydrophobic PLL-DNA. The formation of the complex with free HA was considered essential for directing it to a target cell.

As described above, the present invention relates to the method of targeting a defective bone part in orthopedic surgery, plastic surgery, neurosurgery or dental surgery, and custom-making an artificial bone for the defective bone part in accordance with patient's wish.

In the industrial three-dimensional lamination forming method used for creating a model or a mold, a material containing basic components of a human bone and a cartilage bone is used.

A water insoluble component is mainly used to form a powder layer for lamination, and a water soluble component is jetted through a nozzle to be printed on the lamination powder surface.

An inorganic component such as calcium phosphate which reacts with water or a biocomponent to be solidified, and other bone components are used for the powder layer. A soluble component derived from a bone is dissolved in an aqueous solution liquid phase of the ink jet, and jetted to the powder layer to form a three-dimensional shape, whereby an implantable artificial bone having components similar in nature to those of a bone of a living organism can be formed.

The preferred embodiments of the present invention have been described. However, it can be understood that these embodiments are in no way limitative of a scope of claims of the invention. Conversely, improvements, modifications, equivalents and others are all included in the scope of appended claims of the invention.

The invention claimed is:

1. An artificial bone forming method by a powder lamination method, comprising the steps of:
    (a) forming a powder bone material having biocompatibility, and hardening by hydration, into a flat powder layer;
    (b) jetting an aqueous solution having biocompatibility to a portion of the flat powder layer in order to harden by hydration the portion jetted by the aqueous solution;
    (c) repeating steps (a) and (b) in order to form, by lamination, a specified artificial bone of a predetermined three-dimensional structure in which the hardened portions are connected to each other; and
    (d) after step (c), discharging a gas contained in the artificial bone to further reinforce the hardened portions by a reaction using a change in pressure.

2. The artificial bone forming method by the powder lamination method according to claim 1, wherein
the powder bone material includes an inorganic component, and
the aqueous solution is a liquid mixture, or a suspension of water and a water-soluble biopolymer, wherein the water-soluble biopolymer is a component derived from a living organism.

3. The artificial bone forming method by the powder lamination method according to claim 1, wherein the powder bone material is selected from the group consisting of calcium phosphate, hydroxyapatite, human bone, animal bone, alumina, collagen, polylactic acid, a copolymer of polylactic acid and polyglycolic acid, and a mixture thereof.

4. The artificial bone forming method by the powder lamination method according to claim 1, wherein the aqueous solution comprises a liquid mixture, or a suspension of water and a component selected from the group consisting of soluble collagen, proteoglucan, linkprotein, sodium tartrate, a pH adjuster, a bone growth factor, fibrin, Platelet-Rich Plasma (PRP), a polysaccharide, an amino acid polymer, polylactic acid, a copolymer of polylactic acid and polyglycolic acid, and a mixture thereof.

5. The artificial bone forming method by the powder lamination method according to claim 4, wherein the aqueous solution comprises two or more kinds of liquid mixtures that react with each other in a liquid layer to bring about a hardening reaction, wherein the two or more kinds of liquid mixtures are put in separate vessels and are jetted through a plurality of ink jet nozzles so as to be mixed and hardened at the portion jetted by the aqueous solution.

6. The artificial bone forming method by the powder lamination method according to claim 4, wherein a first component that further promotes a crosslinking reaction, or polymerization of a polymeric component of the artificial bone, is put in a first vessel different from a second vessel for living material to be reacted or polymerized, and the first component is jetted through another ink jet nozzle in order to be mixed at an intended position.

7. The artificial bone forming method by the powder lamination method according to claim 1, wherein a hardening reaction is promoted for the formed artificial bone after step (d), or after step (c), directly under high-temperature and high-pressure water vapor or under a dry high temperature in an autoclave.

8. The artificial bone forming method by the powder lamination method according to claim 2, wherein a hardening reaction is promoted for the formed artificial bone after step (d), or after step (c), directly under high-temperature and high-pressure water vapor or under a dry high temperature in an autoclave.

9. The artificial bone forming method by the powder lamination method according to claim 2, wherein the inorganic component of the powder bone material includes calcium phosphate, and the powder bone material further includes one or more additional components selected from the group consisting of chondroitin sulfate, hyaluronic acid, collagen, pluteogulycan, glycosaminoglycan, deltaman sulfate, heparin sulfate and ketaran sulfate.

10. An artificial bone forming method by a powder lamination method, comprising the steps of:
(a) forming a powder bone material having biocompatibility, and hardening by hydration, into a flat powder layer;
(b) jetting an aqueous solution having biocompatibility to a portion of the flat powder layer in order to harden by hydration the portion jetted by the aqueous solution, wherein the aqueous solution comprises two or more kinds of liquid mixtures that react with each other in a liquid layer to bring about a hardening reaction, wherein the two or more kinds of liquid mixtures are put in separate vessels and are jetted through a plurality of ink jet nozzles so as to be mixed and hardened at a portion jetted by the aqueous solution; and
(c) repeating steps (a) and (b) in order to form, by lamination, a specified artificial bone of a predetermined three-dimensional structure in which the hardened portions are connected to each other.

11. An artificial bone forming method by a powder lamination method, comprising the steps of:
(a) forming a powder bone material having biocompatibility, and hardening by hydration, into a flat powder layer;
(b) jetting an aqueous solution having biocompatibility to a portion of the flat powder layer in order to harden by hydration the portion jetted by the aqueous solution, wherein the aqueous solution comprises a liquid mixture, or a suspension of water and a component selected from the group consisting of soluble collagen, proteoglucan, linkprotein, sodium tartrate, a pH adjuster, a bone growth factor, fibrin, Platelet-Rich Plasma (PRP), a polysaccharide, an amino acid polymer, polylactic acid, a copolymer of polylactic acid and polyglycolic acid, and a mixture thereof; and
(c) repeating steps (a) and (b) in order to form, by lamination, a specified artificial bone of a predetermined three-dimensional structure in which the hardened portions are connected to each other,
wherein a first component that further promotes a crosslinking reaction, or polymerization of a polymeric component of the artificial bone, is put in a first vessel different from a second vessel for living material to be reacted or polymerized, and the first component is jetted through another ink jet nozzle in order to be mixed at an intended position.

12. An artificial bone forming method by a powder lamination method, comprising the steps of:
(a) forming a powder bone material having biocompatibility, and hardening by hydration, into a flat powder layer;
(b) jetting an aqueous solution having biocompatibility to a portion of the flat powder layer in order to harden by hydration the portion jetted by the aqueous solution; and
(c) repeating steps (a) and (b) in order to form, by lamination, a specified artificial bone of a predetermined three-dimensional structure in which the hardened portions are connected to each other, wherein a hardening reaction is promoted for the formed artificial bone after step (c), directly under high-temperature and high-pressure water vapor or under a dry high temperature in an autoclave.

* * * * *